US00PP32832P3

(12) United States Plant Patent
Kai et al.

(10) Patent No.: US PP32,832 P3
(45) Date of Patent: Feb. 23, 2021

(54) ***IPOMOEA BATATAS* PLANT NAMED 'FUKUMURASAKI'**

(50) Latin Name: *Ipomoea batatas*
Varietal Denomination: Fukumurasaki

(71) Applicant: National Agriculture and Food Research Organization, Ibaraki (JP)

(72) Inventors: Yumi Kai, Ibaraki (JP); Akira Kobayahsi, Ibaraki (JP); Takeo Sakaigaichi, Ibaraki (JP); Keisuke Suematsu, Ibaraki (JP); Yasuhiro Takahata, Ibaraki (JP); Masaru Yoshinaga, Ibaraki (JP); Kenji Katayama, Ibaraki (JP); Tetsufumi Sakai, Ibaraki (JP); Toshiro Fujita, Ibaraki (JP)

(73) Assignee: National Agriculture and Food Research Organization, Ibaraki (JP)

( * ) Notice: Subject to any disclaimer, the term of this patent is extended or adjusted under 35 U.S.C. 154(b) by 53 days.

(21) Appl. No.: 16/501,452

(22) Filed: Apr. 16, 2019

(65) Prior Publication Data

US 2019/0320569 P1 Oct. 17, 2019

(30) Foreign Application Priority Data

Apr. 16, 2018 (JP) ..... PBR 33033

(51) Int. Cl.
*A01H 5/06* (2018.01)
*A01H 6/00* (2018.01)
*A01H 5/12* (2018.01)

(52) U.S. Cl.
USPC ..... Plt./258
CPC ..... *A01H 6/00* (2018.05); *A01H 5/06* (2013.01); *A01H 5/12* (2013.01)

(58) Field of Classification Search
USPC ..... Plt./258
CPC ..... A01H 5/06; A01H 6/00
See application file for complete search history.

*Primary Examiner* — Keith O. Robinson
(74) *Attorney, Agent, or Firm* — Mintz, Levin, Cohn, Ferris, Glovsky and Popeo, P.C.

(57) ABSTRACT

'Fukumurasaki' is a new variety of sweet potato plant bred by crossbreeding variety 'Kyukei255' and 'Purple Sweet Lord'. The plant may be used, e.g., for cultivation of root tubers for consumption. The steamed flesh of 'Fukumurasaki' has a purple color, high sugar content, medium to viscous flesh quality, and excellent taste.

3 Drawing Sheets

Plant name and variety denomination:

Latin name of the genus and species of the plant claimed: *Ipomoea batatas*. The claimed plant is a hybridization of different varieties of *Ipomoea batatas*.

Common names of the claimed plant's species: sweet potato.

Variety denomination: 'Fukumurasaki'.

CROSS REFERENCE TO RELATED APPLICATION

The present application claims priority to Japanese Patent Application No. 33033 filed Apr. 16, 2018, the entire contents of which is incorporated herein for all purposes by this reference.

BACKGROUND

*Ipomoea batatas*, commonly called sweet potato or sweet potato vine, is a dicotyledonous plant that belongs to the bindweed or morning glory family, Convolvulaceae. It is an herbaceous perennial that is cultivated for its edible root tubers. *Ipomoea batatas* is native to tropical regions of the Americas.

BRIEF SUMMARY

'Fukumurasaki' is a new variety of *Ipomoea batatas* bred by crossbreeding variety 'Kyukei255' as the female parent and 'Purple Sweet Lord' as the male parent. The plant may be used, e.g., for cultivation of root tubers for consumption. Neither 'Kyukei255' nor 'Purple Sweet Lord' are patented.

'Fukumurasaki' is a purple-colored lineage containing anthocyanins in its storage root. Although the yield of the good quality potatoes is inferior to that of 'Kokei No. 14' and 'Purple Sweet Lord', the steamed flesh of 'Fukumurasaki' has high sugar content, medium to viscous flesh quality, and excellent taste.

The flesh quality of the 'Purple Sweet Lord' is powdery and the sweetness is insufficient compared to the yellow flesh sweet potato. 'Fukumurasaki' has a lower yield of good quality potatoes than 'Kokei No. 14' and 'Purple Sweet Lord,' but has a medium to viscous flesh quality, and taste of the steamed flesh is medium to excellent. Because of the moderate resistance of 'Fukumurasaki' to sweet potato nematodes *Meloidogyne incognita*, cultivation in nematodes-rich areas should be avoided or controlled with pesticide or other measures.

DETAILED BOTANICAL DESCRIPTION OF THE PLANT

Variety: 'Fukumurasaki'

Figure 1A:
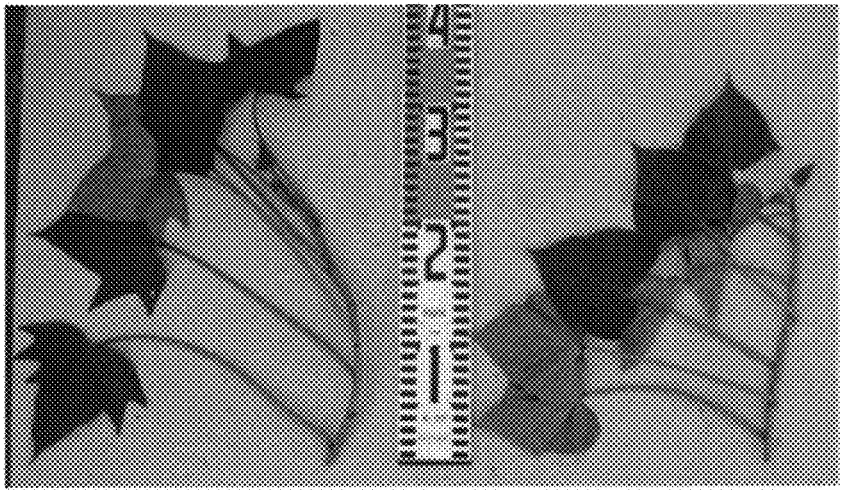
FIG. 1A is a photograph of 'Fukumurasaki' (left) leaves 3 months after planting compared to 'Kokei No. 14' (right).
Figure 1B:
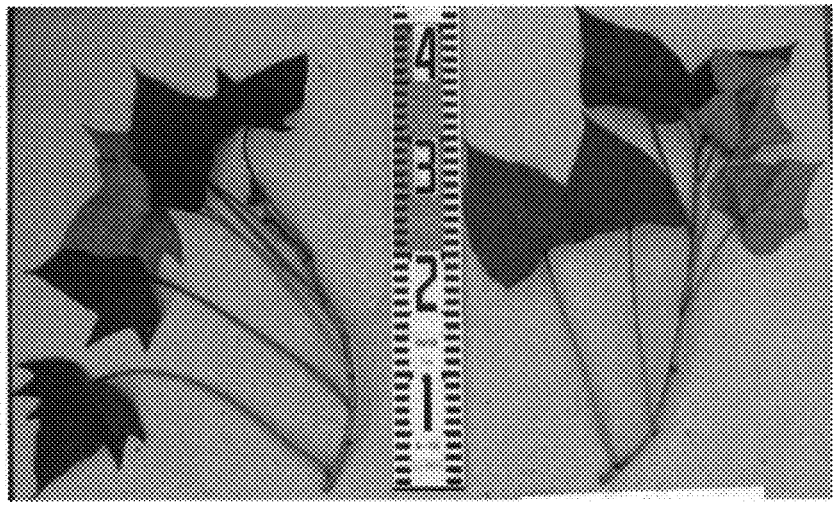
FIG. 1B is a photograph of 'Fukumurasaki' (left) leaves 3 months after planting compared to 'Purple Sweet Lord' (right).
Figure 2A:
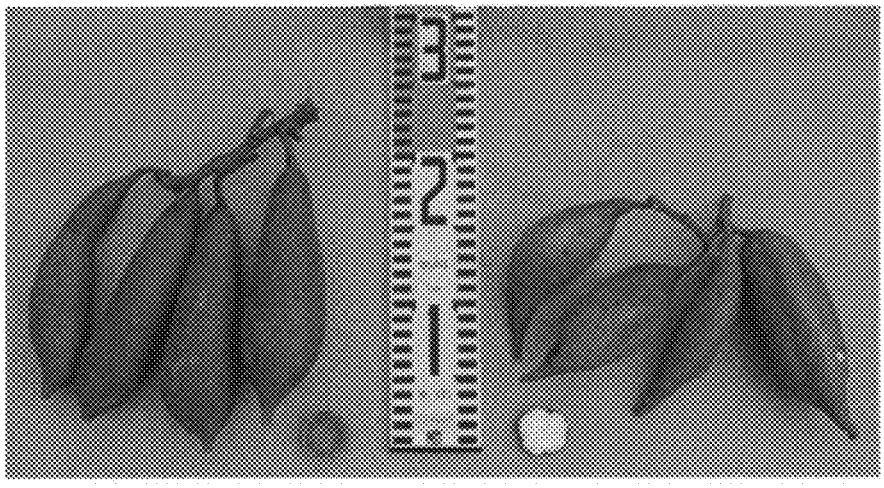
FIG. 2A is a photograph of 'Fukumurasaki' (left) root tuber and cross-section 5 months after planting compared to 'Kokei No. 14' (right).
Figure 2B:
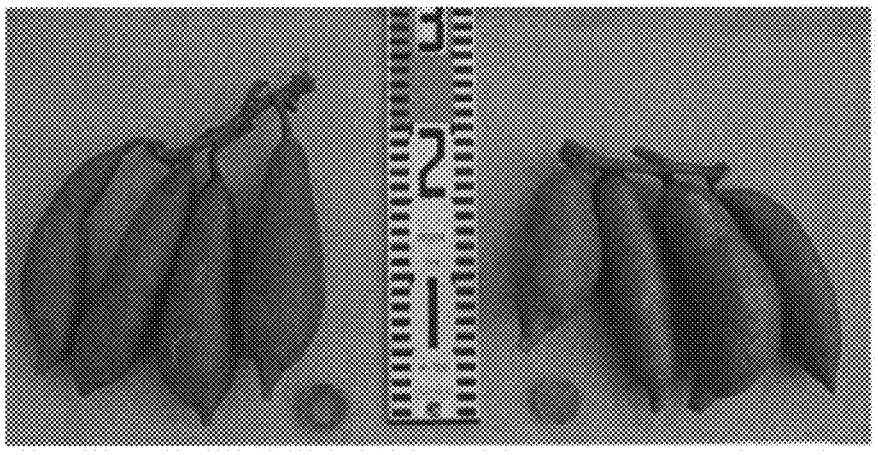
FIG. 2B is a photograph of 'Fukumurasaki' (left) root tuber and cross-section 5 months after planting compared to 'Purple Sweet Lord' (right).
Figure 3:
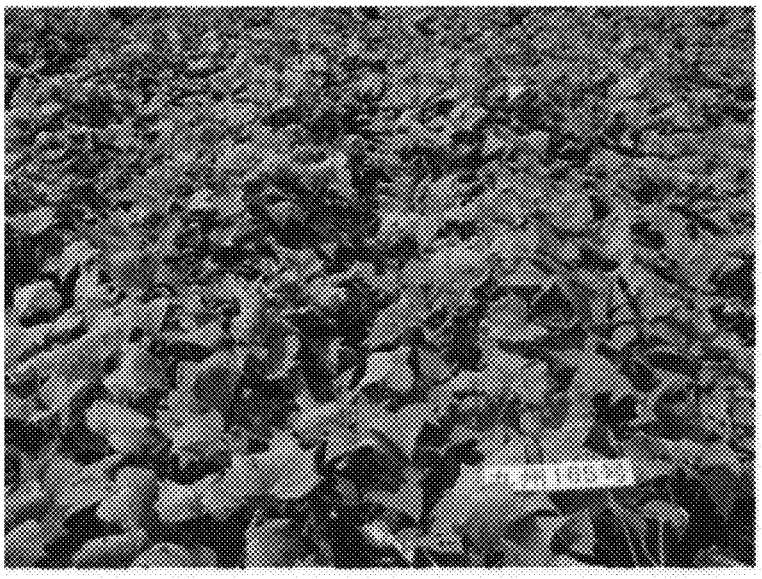
FIG. 3 is a photograph of the cultivation zone of 'Fukumurasaki' 3 months after planting.
Figure 4:
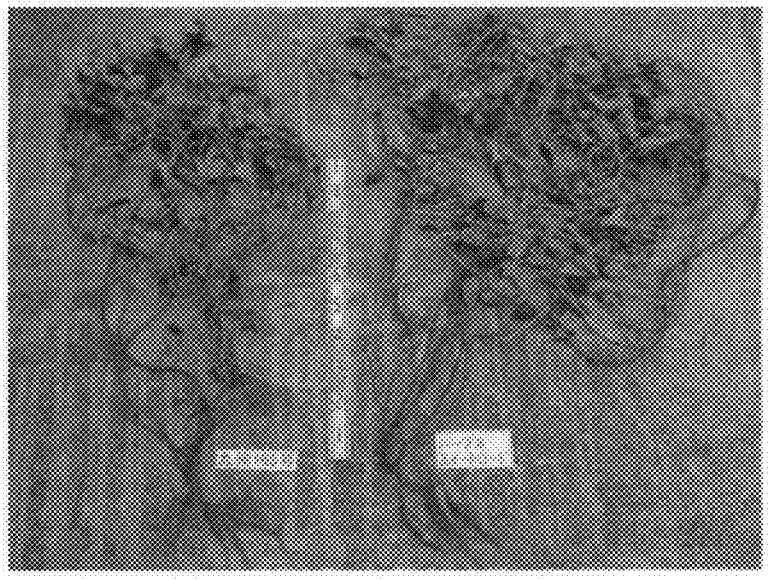
FIG. 4 is a photograph of the whole plant body of Fukumurasaki' (left) 3 months after planting compared to 'Purple Sweet Lord' (right).

Species of the plant claimed: *Ipomoea batatas*. The claimed plant is a hybridization of different varieties. The parental varieties are hybridization of different varieties.

Common names of the claimed plant's species include: sweet potato.

Characteristics of 'Fukumurasaki' provided herein were observed when the plant was cultivated in Okinawa and Satsuma, Japan. Descriptive terms used in Table 1 are consistent with the Japanese Examination Standard for *Ipomoea batatas*, available at website hinshu2.maff.gojp/info/sinsakijun/kijun/1347.pdf, the entire contents of which are incorporated herein by reference.

Properties and characteristics of 'Fukumurasaki', compared to the most similar varieties, are described in Table 1. For designated colors, the recognized color dictionary or color chart used is the Fifth Edition (2007) of "The Royal Horticulture Society Color Chart (R.H.S.)."

TABLE 1

Properties and characteristics of 'Fukumurasaki'

| Characteristic No. | Characteristics | Class values of candidate variety 'Fukumurasaki' | Remarks (Measurement Value etc.) | Class Values of most similar varieties 'Kokei No. 14' | Class Values of most similar varieties 'Purple Sweet Lord' |
|---|---|---|---|---|---|
| 1 | Plant: growth habit | semi-upright | | spreading | spreading |
| 2 | Stem: length of primary shoots and lateral branch | short | 46.8 cm | medium (106.2 cm) | long (157.4 cm) |
| 3 | Stem: length of internode and lateral branch | short | 2.6 cm | medium (5.1 cm) | long (8.5 cm) |
| 4 | Stem: diameter of internode and lateral branch | large | 7.65 mm | medium to large (6.50 mm) | medium to large (6.67 mm) |
| 5 | Stem: anthocyanin coloration of internode and lateral branch | weak | | absent or very weak | weak |
| 6 | Stem: anthocyanin coloration of tip and lateral branch | weak | | absent or very weak | weak |
| 7 | Stem: anthocyanin coloration of node and lateral branch | medium | | absent or very weak | strong |
| 8 | Stem: pubescence of tip | dense | | sparse | sparse |
| 9 | Leaf blade: size | large | 250.1 $cm^2$ | medium (160.9 $cm^2$) | medium to large (218.7 $cm^2$) |
| 10 | Leaf blade: number of lobes | five lobes | | absent | absent |
| 11 | Only varieties without leaf blade lobes: Leaf blade: shape | — | | cordate | triangular |
| 12 | Only varieties with leaf blade lobes: Leaf blade: depth of lobing | moderate | | — | — |
| 13 | Excluding ornamental variety: Leaf blade: color on upper side (excluding anthocyanin coloration) | green | 136A of RHS | Green (136B of RHS) | Green (136B of RHS) |
| 19 | Excluding ornamental variety: Leaf blade: anthocyanin coloration on upper side | absent or very weak | | absent or very weak | absent or very weak |
| 20 | Leaf blade: extent of anthocyanin coloration on abaxial veins on lower side | absent or very small | | small | large |
| 21 | Leaf blade: intensity of anthocyanin coloration on abaxial veins on lower side | very weak | | very weak | weak |
| 22 | Leaf blade: anthocyanin coloration of nectary | absent or very weak | | absent or very weak | strong |
| 23 | Young leaf blade: main color on upper side | dark green | N189A of RHS | light green (137A of RHS) | dark green (N189A of RHS) |
| 24 | Young leaf blade: main color on lower side | medium green | N137A of RHS | light green (138A of RHS) | medium green (N137A of RHS) |

TABLE 1-continued

Properties and characteristics of 'Fukumurasaki'

| Characteristic No. | Characteristics | Class values of candidate variety 'Fukumurasaki' | Remarks (Measurement Value etc.) | Class Values of most similar varieties | |
|---|---|---|---|---|---|
| | | | | 'Kokei No. 14' | 'Purple Sweet Lord' |
| 25 | Petiole: anthocyanin coloration | absent or very weak | | absent or very weak | absent or very weak |
| 26 | Petiole: length | medium | 24.4 cm | medium (22.4 cm) | medium to long (26.7 cm) |
| 27 | Corolla: diameter | — | | — | — |
| 28 | Corolla: color | — | | — | — |
| 29 | Storage root: shape | ovate | | elliptic | oblong |
| 30 | Storage root: ratio length/width | moderately elongated | 4.6 | moderately elongated (4.0) | medium (2.9) |
| 31 | Storage root: number | medium | 3.8 storage roots/plant | medium (3.1 storage roots/plant) | medium (3.9 storage roots/plant) |
| 32 | Storage root: mean weight | medium | 142 g | medium (146 g) | medium to large (182 g) |
| 33 | Storage root: thickness of cortex relative to overall diameter | thick | 0.072 | medium (0.055) | medium (0.052) |
| 34 | Storage root: main color of skin | purple red | 59C of RHS | red (182A of RHS) | purple red (71B of RHS) |
| 35 | Storage root: secondary color of skin | absent | | absent | absent |
| 36 | Storage root: main color of flesh | purple | N77B of RHS | light beige (155D of RHS) | Purple (71C of RHS) |
| 37 | Storage root: intensity of main color of flesh | medium | | medium | medium |
| 38 | Storage root: secondary color of flesh | white | N155B of RHS | — | White (N155B of RHS) |
| 39 | Storage root: depth of eyes | shallow | | medium | medium |
| 40 | Storage root: color of steamed flesh | purple | N186B of HRS | light beige (2C of RHS) | light purple (79D of RHS) |
| 41 | Southern root-knot nematode (*Pratylenchus caffeae*) resistance | moderately strong | | moderately weak | strong |
| N/A | Original color of lateral branch | Green | 138B of RHS | Green (138B of RHS) | Green (138B of RHS) |
| N/A | Length of Leaf | | 15.9 cm | 13.0 cm | 15.5 cm |
| N/A | Width of Leaf | | 15.7 cm | 12.3 cm | 14.0 cm |
| N/A | Original color of petiole | Green | 138B of RHS | Green (138B of RHS) | Green (138B of RHS) |

Cross-breeding was carried out in 2004 in Miyazaki prefecture, Japan. From 2005 onwards, selection and breeding were carried out in Japan. Based on the result of seedling individual selection test in 2005, a lineage was selected which showed excellent in appearance and root tuberization, and gave the lineage number of 'Kyukei 04008-3'. Thereafter, they were used for the lineage selection preliminary test in 2006, the lineage selection test in 2007, and the productivity check preliminary test in 2008. As a result of examining various characteristics, we selected a lineage with excellent color of flesh and excellent characteristics of the steamed flesh, from 'Kyukei 04008-3', and gave the lineage number of 'Kyukei 288'. And, since 2009, a productivity check test, a lineage adaptability test (Nagasaki, Ehime, etc.), a black rot (*Ceratocystis fimbriata*) resistance test (Nagasaki), and a damping-off resistance test (Tokushima) have been carried out, with the lineage number of 'Kyukei 288'. Finally, 'Fukumurasaki' was selected by comprehensively examining the results of these tests.

Morphological Characteristic

The plant growth habit in a field is the "semi-upright" type, and length of primary shoots and the length of internode of the stem are shorter and the diameter of internode is slightly larger than the 'Kokei No. 14' and the 'Purple Sweet Lord'.

The coloration of 'Fukumurasaki' internode is "weak" and the coloration of node is "weak to medium", the color on upper side of young leaf is "dark green" (N189A of RHS) and the color on back side of young leaf is "green" (N137A of RHS), the leaf color is "green" (136A of RHS), the leaf size is "large", the number of lobes in leaf blade is "5", and the leaf shape according to the old reference is "double-incision".

The extent of the coloration on abaxial veins on lower side of the leaf is "absent or very small", the intensity of the coloration of the same is "very weak", and the coloration of the nectary is "absent or very weak". The arrangement of the leaves is alternate.

The strength of the storage root's neck and the position of the storage root (same as depth from the field surface to storage root) are "medium", and the difficulty of digging (harvesting) the storage root (same as root tuber) is "medium". The shape of storage root is "ovate" in the new standard and "long spindle" in the old standard.

Shape regularity of storage roots is "moderate"; size of storage roots is "medium"; size regularity of storage roots is "medium", mean length of storage roots is 19.7 cm±3.0 cm and mean width of storage roots is 4.4 cm±0.4 cm; skin color of storage root is "purple red" (59C of RHS); flesh color is "purple" (N77B of RHS); depth of eye in storage root is "shallow"; skin roughness of storage root is "slightly coarse"; grooves and ridges of storage root are "absent"; dehiscence of storage root is "little"; appearance is "medium".

At earlier harvest timing under cultivation with mulching sheet, the total weight of good quality storage roots of 'Fukumurasaki' is about 60% of that of 'Kokei No. 14'. Under later-planting-timing cultivation without mulching sheet, the total weight of good quality storage roots is about 60% of that of 'Kokei No. 14'. The mean weight of one good quality storage roots is lower than that of 'Kokei No. 14'. The number of good quality storage roots per one plant is equivalent to that of 'Kokei No. 14'. The percentage of dry matter content is about 5 points higher (at the earlier harvest timing), and about 7 points higher (under later-planting-timing cultivation) than those of 'Kokei No. 14'. Table 2 below contains mean numerical values for characteristics of the good quality storage roots.

TABLE 2

| Cultivation method | Characteristic | 'Fuku-murasaki' | 'Kokei No. 14' | 'Purple Sweet Lord' |
|---|---|---|---|---|
| Standard cultivation with black mulching sheet | Weight of the good quality storage roots | 201 kg/a | 249 kg/a | — |
| | Mean weight of one good quality storage root | 127 g | 192 g | 194 g |
| | No. of good quality storage roots per plant | 4.2 | 3.5 | 4.2 |
| | Percentage of dry matter content | 37.2% | 31.6% | — |
| Cultivation with transparent mulching sheet at earlier harvest timing | Weight of the good quality storage roots | 104 kg/a | 163 kg/a | — |
| | Mean weight of one good quality storage root | 85 g | 131 g | — |
| | No. of good quality storage roots per plant | 3.1 | 3.3 | — |
| | Percentage of dry matter content | 36.4% | 31.5% | — |
| Later-planting timing cultivation without mulching | Weight of the good quality storage roots | 107 kg/a | 173 kg/a | — |
| | Mean weight of one good quality storage root | 106 g | 154 g | — |
| | No. of good quality storage roots per plant | 2.7 | 3.0 | — |
| | Percentage of dry matter content | 34.6% | 27.6% | — |

Ecological Characteristics

The timing (early or late) of sprouting of 'Fukumurasaki' from storage root, the timing regularity of sprouting from different storage roots (almost simultaneous or not), the speed of sprout elongation, and the number of sprouts are "medium", mean numerical value 8-10 sprouts, and the sprouting trait (same as sprouting habit) is "medium".

On average, the total weight of the good quality storage roots is 19% lower than that of 'Kokei No. 14'. The mean weight of one good quality storage roots is lower than that of 'Kokei No. 14' and 'Purple Sweet Lord'. The number of good quality storage roots per one 'Fukumurasaki' plant is slightly larger than that of the 'Kokei No. 14' and equivalent to that of the 'Purple Sweet Lord'. The percentage of dry matter content is about 5.6 points higher than that of 'Kokei No. 14'.

The resistance of 'Fukumurasaki' to sweet potato nematodes (*M. incognita*) is "medium" and the resistance to Minami root-lesion nematodas (*P. coffeae*) is "moderately strong". The resistance to black rot (*Ceratocystis fimbriata*) disease is "medium to strong". The resistance to damping-off is "slightly weak to slightly strong", and the resistance to stem rot (*Fusarium oxysporum* f, sp. *batatas*) is "strong". Storability of storage root is "medium".

Regarding temperature tolerance of 'Fukumurasaki,' the preferable temperature for growth is 16 degrees Celsius or higher. More preferably, the temperature for growth is 20-35 degrees Celsius. Temperatures under 9 degrees Celsius can sometimes cause low-temperature damage to the plant.

Quality Characteristics and Processability

In standard cultivation, the steamed flesh color of the 'Fukumurasaki' storage root is "purple" (N186B of RHS), fibers in steamed flesh is "medium", and the quality of flesh is "medium". The taste of steamed or roasted storage root is "somewhat superior" and Brix is higher than 'Kokei No. 14' and 'Purple Sweet Lord'.

Other Characteristics

Brix of 'Fukumurasaki' steamed storage root is higher than 'Kokei No. 14' and 'Purple Sweet Lord' in both the cultivation with transparent mulching sheet at earlier harvest timing and the later-planting-timing cultivation without mulching. For standard cultivation with black mulching sheet, Brix numerical values are as follows. Brix for steamed storage root is 24.8% for 'Fukumurasaki,' 16.6% for 'Kokei No. 14,' and 13.4% for 'Purple Sweet Lord.' Brix for roasted storage root is 24.7% for 'Fukumuraksi,' 17.5% for 'Kokei No. 14,' and 14.7% for 'Purple Sweet Lord.' For cultivation with transparent mulching sheet at earlier harvest timing, Brix numerical values are as follows. Brix for steamed storage root is 19.6% for 'Fukumurasaki,' 16.3% for 'Kokei No. 14,' and 13.8% for 'Purple Sweet Lord.' For later-planting-timing cultivation without mulching, Brix numerical values are as follows. Brix for steamed storage root is 19.5% for 'Fukumurasaki,' 15.3% for 'Kokei No. 14,' and 16.2% for 'Purple Sweet Lord.'

The taste of 'Fukumurasaki' steamed storage root is "medium" under the cultivation with transparent mulching sheet at earlier harvest timing, and "slightly higher" under the later-planting-timing cultivation without mulching.

In October, 2016, samples (storage roots) cultivated in the field in the city of Namegata were stored for about 70 days, and then each sample was roasted at 200° C. for 1 hour to prepare roasted samples (roasted sweet potatoes), and sensory evaluation by panelists was carried out. 'Fukumurasaki' was more viscous than 'Purple Sweet Lord' in terms of roasted flesh quality, superior in texture and sweetness, and 'Fukumurasaki' exceeded 'Purple Sweet Lord' in overall evaluation.

'Fukumurasaki' was grown in open culture. In Japan, planting occurs in the early part of May to the end part of May. In Japan harvesting time is the middle part of October to the end part of October.

It will be understood that the average size of the plant and storage root may vary with location, season, nutrition, irrigation, etc.

What is claimed is:

1. A new and distinct *Ipomoea batatas* plant named 'Fukumurasaki' as illustrated and described.

* * * * *